(12) United States Patent
Fukuzono (10) Patent No.: US 7,790,368 B1
(45) Date of Patent: Sep. 7, 2010

(54) METHOD FOR ANALYZING NUCLEIC ACID

(75) Inventor: Shinichi Fukuzono, Hitachinaka (JP)

(73) Assignee: Hitachi, Ltd., Tokyo (JP)

( * ) Notice: Subject to any disclaimer, the term of this patent is extended or adjusted under 35 U.S.C. 154(b) by 0 days.

(21) Appl. No.: 09/958,727

(22) PCT Filed: Sep. 22, 2000

(86) PCT No.: PCT/JP00/06526

§ 371 (c)(1),
(2), (4) Date: Oct. 10, 2001

(87) PCT Pub. No.: WO02/24949

PCT Pub. Date: Mar. 28, 2002

(51) Int. Cl.
*C12Q 1/68* (2006.01)
*C07H 21/02* (2006.01)
*C07H 21/04* (2006.01)

(52) U.S. Cl. .................... 435/6; 536/23.1; 536/24.3
(58) Field of Classification Search .................... 435/6, 435/91.1, 91.2; 536/23.1
See application file for complete search history.

(56) References Cited

U.S. PATENT DOCUMENTS

| | | | |
|---|---|---|---|
| 5,096,557 A | | 3/1992 | Simons |
| 5,789,153 A | * | 8/1998 | Falkner et al. |
| 5,858,658 A | * | 1/1999 | Haemmerle et al. |
| 5,888,740 A | * | 3/1999 | Han |
| 6,001,572 A | * | 12/1999 | Toothman |
| 6,258,536 B1 | * | 7/2001 | Oliner et al. ................... 435/6 |
| 6,544,777 B1 | * | 4/2003 | Schrenzel et al. ........ 435/287.2 |

FOREIGN PATENT DOCUMENTS

| | | |
|---|---|---|
| EP | 0 466 479 A1 | 1/1992 |
| EP | 0 714 988 A2 | 6/1996 |
| JP | 8-501222 | 2/1996 |
| WO | WO 95-02067 | 1/1995 |
| WO | WO-95/02067 | 1/1995 |
| WO | WO 99/02728 | 1/1999 |
| WO | WO-99/14371 | 3/1999 |

OTHER PUBLICATIONS

Ursi et al., Utility of an internal control for the polymerase chain reaction. APMIS 100 : 635-639 (1992).*
The USB Catalog, "Basic DNA Analysis Kit" p. 103 (1988).*
Orita et al., Rapid and sensitive detection of point mutations and DNA polymorphisms using the polymerase chain reaction. Genomics 5 :874-879 (1989).*
Peter Friedhoff, et al., "Quantitative Polymerase Chain Reaction with Oligodeoxynucleotide Ligation Assay/Enzyme-Linked Immunosorbent Assay Detection," 2247 Analytical Biochemistry, 215 (1993) Nov. 15, No. 1, Orlando, FL, pp. 9-16.

* cited by examiner

*Primary Examiner*—Ethan Whisenant
(74) *Attorney, Agent, or Firm*—Dickstein Shapiro LLP (57) ABSTRACT

A method is provided for analyzing nucleic acid comprising the steps of extracting, amplifying and detecting the nucleic acid of interest, wherein one or more internal control nucleic acids which can be detected and discriminated from the nucleic acid of interest are added for each step to a sample prior to the performance of each step, and the success or failure of each step is judged from the detection results obtained for the respective internal control nucleic acids in the detection step. The internal control nucleic acids added prior to each step can be discriminated from each other.

8 Claims, 10 Drawing Sheets

Fig. 1

| case | extraction IC | detection IC | judgement | required reanalysis |
|---|---|---|---|---|
| 1 | normal | normal | success | — |
| 2 | normal | abnormal /not detected | not determined | 3 |
| 3 | abnormal /not detected | normal | insufficient extraction | 1 |
| 4 | abnormal /not detected | abnormal /not detected | insufficient | 1 or 3 | extraction IC : internal control nucleic acid for extraction
detection IC : internal control nucleic acid for detection

| case | extraction IC | amplification IC | detection IC | judgement | required reanalysis |
|---|---|---|---|---|---|
| 1 | normal | normal | normal | success | — |
| 2 | normal | normal | abnormal /not detected | not determined | 3 |
| 3 | normal | abnormal /not detected | normal | not determined | 2 |
| 4 | normal | abnormal /not detected | abnormal /not detected | not determined | 2 |
| 5 | abnormal /not detected | normal | normal | insufficient extraction | 1 |
| 6 | abnormal /not detected | normal | abnormal /not detected | insufficient extraction | 1 |
| 7 | abnormal /not detected | abnormal /not detected | normal | insufficient extraction /amplification | 1 |
| 8 | abnormal /not detected | abnormal /not detected | abnormal /not detected | insufficient | 3 or 1 | extraction IC : internal control nucleic acid for extraction
amplification IC : internal control nucleic acid for amplification
detection IC : internal control nucleic acid for detection

Fig. 4

Fig. 6 normal abnormal 1 abnomal 2

Fig. 8A before data processing

Fig. 8B after data processing

METHOD FOR ANALYZING NUCLEIC ACID

TECHNICAL FIELD

The present invention relates to a method for analyzing nucleic acid, and a kit for performing the method. More particularly, the method of the present invention comprises the steps of extracting, detecting and in some cases amplifying the nucleic acid of interest. In this method, at least one internal control nucleic acid that can be detected separately from the nucleic acid of interest is used for each step and treated simultaneously with the nucleic acid of interest. The success or failure of each step is judged from the detection results obtained for the internal control nucleic acids, and reanalysis may be performed on the basis of the results of the judgement.

BACKGROUND ART

The isolation and analysis of genes from samples of living organisms is an extremely effective means of performing research in the field of molecular biology. In the medical field as well, such analysis is widely used. In the past, numerous genes have been isolated and identified from living organisms and tissues for the purpose of genetic analysis. Furthermore, the polymerase chain reaction (PCR) method (Science: Vol. 239, pp. 487-491 (1988)) has been developed as a gene amplification method, and has made it possible to isolate and detect genes that are present in extremely small amounts. Furthermore, human genome analysis has developed rapidly, and associations between genetic mutations such as single-nucleotide polymorphism or the like and diseases or drug reactions have received attention. The utilization of such genetic polymorphism is not limited to molecular biology and genetics; it is expected that such polymorphism will be utilized in made-to-order therapy and drug administration in the field of medical diagnosis.

A typical gene analysis process comprises an extraction step and a detection step of the nucleic acid of interest from a sample; and optionally comprises a nucleic acid amplification step between the extraction step and the detection step.

A method that is widely known as a nucleic acid extraction method is the so-called protease K/phenol method (Molecular Cloning: A Laboratory Manual, Appendix E3-E4 (New York: Cold Spring Harbor Laboratory, 1989)), in which nucleic acids are liberated by destroying cells and breaking down proteins through the addition of a proteolytic enzyme such as protease K or the like, and a surfactant, after which phenol/chloroform is added, the nucleic acid is distributed into the aqueous phase by centrifugation, and ethanol, isopropanol or the like is added to the recovered aqueous phase so that the nucleic acid becomes insolubilized. However, this method is not suitable for automation, since it involves centrifugation step and the like. In order to solve such problems, methods that utilize the adsorption characteristics of nucleic acids on a solid phase have been proposed. For example, the bonding of nucleic acids to glass in the presence of chaotropic salts has been reported (Proc. Natl. Acad. Sci. USA 76, 615-619 (1979)). By applying such characteristics of nucleic acid bonding to silicon oxide (silica) under certain conditions, nucleic acid extraction kits and automated nucleic acid extraction devices based on magnetic silica particles, silica particles, silica fibers or filters, and spin columns, microplates or the like containing these substances, were disclosed (Japanese Patent Application Laid-Open (kohyo) No. H10-504834, Japanese Patent Application Laid-Open (kohyo) No. H9-505724, Japanese Patent Application Laid-Open (kokai) No. H8-320274, Japanese Patent Application Laid-Open (kokai) No. H9-304385, Japanese Patent Examined Publication (kokoku) No. 2807090).

In regard to methods used for nucleic acid detection step, and especially in regard to methods for detecting nucleic acids whose sequences differ by one or more nucleotides, single-stranded DNA conformational polymorphism (SSCP) or restriction enzyme fragment length polymorphism (RFLP) using gel electrophoresis, and microarray methods, DNA chip methods and bead array methods in which a single-stranded nucleic acid is fixed on glass, silicon wafers or various types of beads, and hybridization with the object nucleic acid is detected, as well as pyro-sequencing methods, invader methods, mass spectrometry methods, HPLC methods and the like have been developed and are widely utilized.

As nucleic acid amplification methods, polymerase chain reactions (PCR) (U.S. Pat. No. 4,683,195 and U.S. Pat. No. 4,683,202), nucleic acid sequence-based amplification (NASBA) (European Patent NO. 0, 329, 822) and the like are known and utilized. Furthermore, nucleic acid determination methods using competitive amplification or co-amplification are generally known. In such methods, several types of internal control nucleic acids which react with the same primer as the nucleic acid of interest are subjected to an amplification reaction in the same vessel, and the amount of the nucleic acid of interest is determined using the known quantities of the internal control nucleic acids as a reference (Japanese Patent Application Laid-Open (kohyo) No. H8-107798, Japanese Patent Application Laid-Open (kohyo) No. H8-501222, Japanese Patent Application Laid-Open (kohyo) No. H11-123095, Japanese Patent Application Laid-Open (kohyo) No. H11-506613).

For the most part, such conventional techniques are utilized exclusively for the determination of the amount of the object nucleic acid of interest based on a process in which a fixed amount of a nucleic acid which can be detected while being discriminated from the nucleic acid of interest, and which is generally referred to as an internal control nucleic acid or the like, is amplified simultaneously with the nucleic acid of interest in the nucleic acid amplification step. In these methods, it is assumed throughout that the nucleic acid of interest has been prepared normally (Japanese Patent Application Laid-Open (kohyo) No. H8-107798, Japanese Patent Application Laid-Open (kohyo) No. H11-123095, Japanese Patent Application Laid-Open (kohyo) No. H11-506613). On the other hand, a method which reflects the extraction efficiency of the object nucleic acid in the extraction step, and a method for detecting cross-contamination between samples are described in Japanese Patent Application Laid-Open (kohyo) No. H8-501222. However, it is essential that the methods include a nucleic acid amplification step, and it is difficult to judge the success or failure of the overall series of nucleic acid analysis steps and/or to ascertain in which step an abnormality has occurred.

Accordingly, it is an object of the present invention to provide a method for analyzing a nucleic acid, whose aim is to ensure or improve the reliability of the analysis results obtained in the analysis of nucleic acids.

DISCLOSURE OF THE INVENTION

The present invention provides a method for analyzing a nucleic acid which comprises the steps of extracting and detecting the nucleic acid of interest, and which in some cases further comprises a step of amplification that is performed between the extraction step and the detection step, wherein one or more internal control nucleic acids which can be detected while being discriminated from the nucleic acid of interest and internal control nucleic acids used in other steps are added to the sample prior to the execution of the respective steps, after which the respective steps are performed in the same vessel with the object nucleic acid, and the success or failure of the respective steps is judged from the detection results obtained for the respective internal control nucleic acids in the nucleic acid detection step.

Specifically, the present invention provides a method for analyzing a nucleic acid comprising the steps of extracting and detecting the nucleic acid of interest, wherein the step of extracting nucleic acids is performed after one or more internal control nucleic acids for extraction which can be detected while being discriminated from the nucleic acid of interest have been added, and judging the success or failure of the extraction step from the detection results obtained for the abovementioned internal control nucleic acids.

Furthermore, the present invention provides a method for analyzing a nucleic acid comprising the steps of extracting and detecting the nucleic acid of interest, wherein the steps of extracting and detecting are performed after one or more internal control nucleic acids for extraction and internal control nucleic acids for detection which can be detected while being discriminated from the nucleic acid of interest and from each other have been added, and judging the success or failure of the extraction step and detection step from the detection results obtained for the abovementioned internal control nucleic acids.

Furthermore, the present invention provides a method for analyzing a nucleic acid comprising the steps of extracting, amplifying and detecting the nucleic acid of interest, wherein the steps of extracting and detecting are performed after one or more internal control nucleic acids for extraction, internal control nucleic acids for amplification and internal control nucleic acids for detection, which can be detected respectively while being discriminated from the nucleic acid of interest and from each other, have been added, and judging the success or failure of the steps of extracting and detecting from the detection results obtained for the abovementioned internal control nucleic acids.

Furthermore, the present invention provides a method for analyzing a nucleic acid comprising the steps of extracting and detecting the nucleic acid of interest, which is characterized in that the method comprises:
  (a) a nucleic acid extraction step in which nucleic acids are extracted after one or more internal control nucleic acids for extraction which can be detected while being discriminated from the nucleic acid of interest have been added to a sample containing the nucleic acid of interest,
  (b) a nucleic acid detection step in which nucleic acids are detected after one or more internal control nucleic acids for detection which can be detected while being discriminated from the abovementioned nucleic acid of interest and internal control nucleic acids for extraction have been added to a sample containing the nucleic acids extracted in the abovementioned step (a), and
  (c) a step in which the success or failure of the abovementioned respective steps is judged from the detection results obtained for the abovementioned respective internal control nucleic acids.

Furthermore, the present invention provides a method for analyzing a nucleic acid comprising the steps of extracting, amplifying and detecting the nucleic acid of interest, which is characterized in that the method comprises:
  (a) a nucleic acid extraction step in which nucleic acids are extracted after one or more internal control nucleic acids for extraction which can be amplified simultaneously with the nucleic acid of interest, but which can be detected while being discriminated from the nucleic acid of interest, have been added to a sample containing the nucleic acid of interest,
  (b) a nucleic acid amplification step in which nucleic acids are amplified after one or more internal control nucleic acids for amplification which can be amplified simultaneously with the nucleic acid of interest and the internal control nucleic acids for extraction, but which can be detected while being discriminated from the nucleic acid of interest and the internal control nucleic acids for extraction, have been added to a sample containing the nucleic acids extracted in the above-mentioned step (a),
  (c) a nucleic acid detection step in which nucleic acids are detected after one or more internal control nucleic acids for detection, which can be detected while being discriminated from the nucleic acid of interest, the internal control nucleic acids for extraction and the internal control nucleic acids for amplification, have been added to a sample containing the nucleic acids amplified in the above-mentioned step (b), and
  (d) a step in which the success or failure of the above-mentioned respective steps is judged from the detection results obtained for the above-mentioned respective internal control nucleic acids.

Furthermore, the method for analyzing a nucleic acid of the present invention is characterized in that analysis may be reperformed from any one of the steps on the basis of the results of the above-mentioned judgment of the success or failure of the extraction, amplification or detection step.

Figure 1:
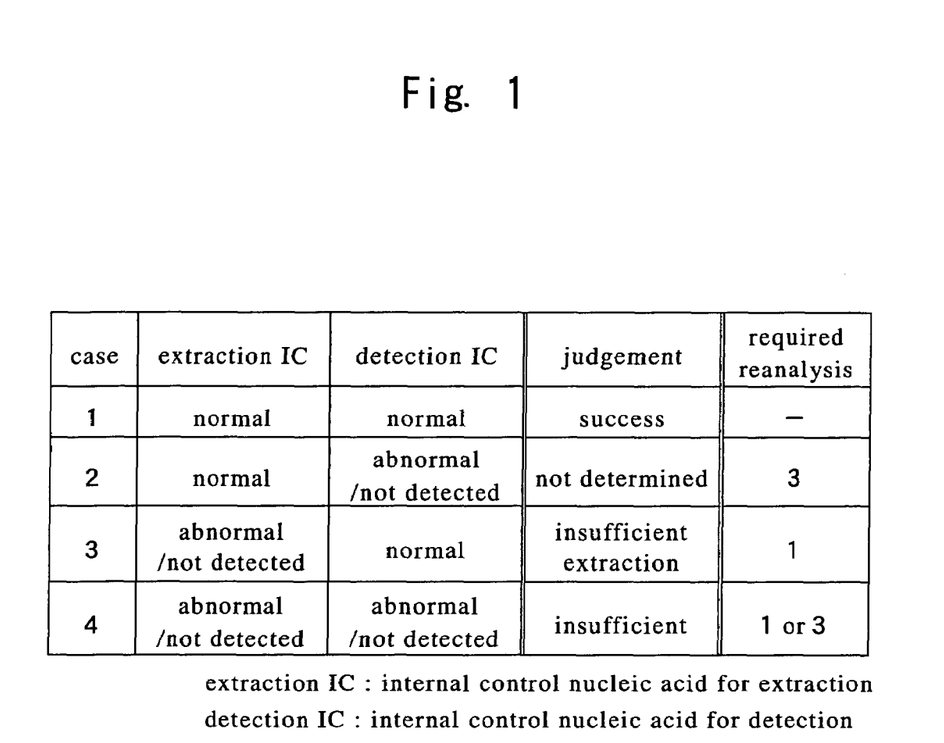
FIG. 1 shows a table for success-or-failure determination for the respective steps in the method of the present invention that includes an extraction step and a detection step.

Specifically, a fixed amount of an internal control nucleic acid for extraction whose sequence differs by one or more nucleotides from that of the nucleic acid of interest is added to a sample containing the nucleic acid of interest. Then, a nucleic acid extraction step is performed, and a fixed amount of an internal control nucleic acid for detection, whose sequence differs by one or more nucleotides from those of the nucleic acid of interest and the internal control nucleic acid for extraction, is added to the nucleic acid extract thus obtained, and a known nucleic acid detection step, which is capable of detecting and discriminating between nucleic acids whose sequences differ by one or more nucleotides, is performed. As a result, the success or failure of the respective steps is judged as shown in FIG. 1, and the need for reanalysis is determined based on the results of the judgement. Furthermore, false positives caused by sample contamination can be checked by treating a sample that contains no object nucleic acid (i.e., a blank sample) simultaneously with the object sample, and it facilitates the judgement of the need for reanalysis. In this case, it is judged that contamination has occurred if the object nucleic acid is detected in the blank sample, and analysis should be re-performed following a cleaning operation regardless of the detection results obtained for the internal control nucleic acid(s) for extraction and internal control nucleic acid(s) for detection.

Below, the judgements made in cases where the detection results obtained for the internal control nucleic acid(s) for extraction and the internal control nucleic acid(s) for detection are normal and cases where these detection results are not normal, and the steps that must be re-performed in cases where the detection results are not normal, will be described with reference to FIG. 1.

Case 1 (A Case in which Both the Detections of the Internal Control Nucleic Acid(s) for Extraction and Those of the Internal Control Nucleic Acid(s) for Detection are Normal)

It is judged that the respective steps were performed normally, and that the nucleic acid analysis operation performed for the nucleic acid of interest was "success".

Case 2 (A Case in which the Detections of the Internal Control Nucleic Acid(s) for Extraction are Normal, While the Detections of the Internal Control Nucleic Acid(s) for Detection are Abnormal, or the Latter Nucleic Acids are not Detected)

In cases where the nucleic acid of interest is not detected in the blank sample, it is highly probable that the nucleic acid analysis operation for the nucleic acid of interest itself was performed normally. However, there is a possibility that the internal control nucleic acid(s) for detection and/or the addition mechanism of them may be abnormal. Consequently, such cases are judged as "not determined". Accordingly, the internal control nucleic acid(s) for detection should be replaced, or the addition mechanism of them is inspected, or both of these measures are taken, and the analysis is re-performed from the point "reanalysis 3" (backward arrow) shown in FIG. 2.

Case 3 (A case in which the Detections of the Internal Control Nucleic Acid(s) for Extraction are Abnormal, or they can not be Detected, While the Detections of the Internal Control Nucleic Acid(s) for Detection are Normal)

Figure 2:
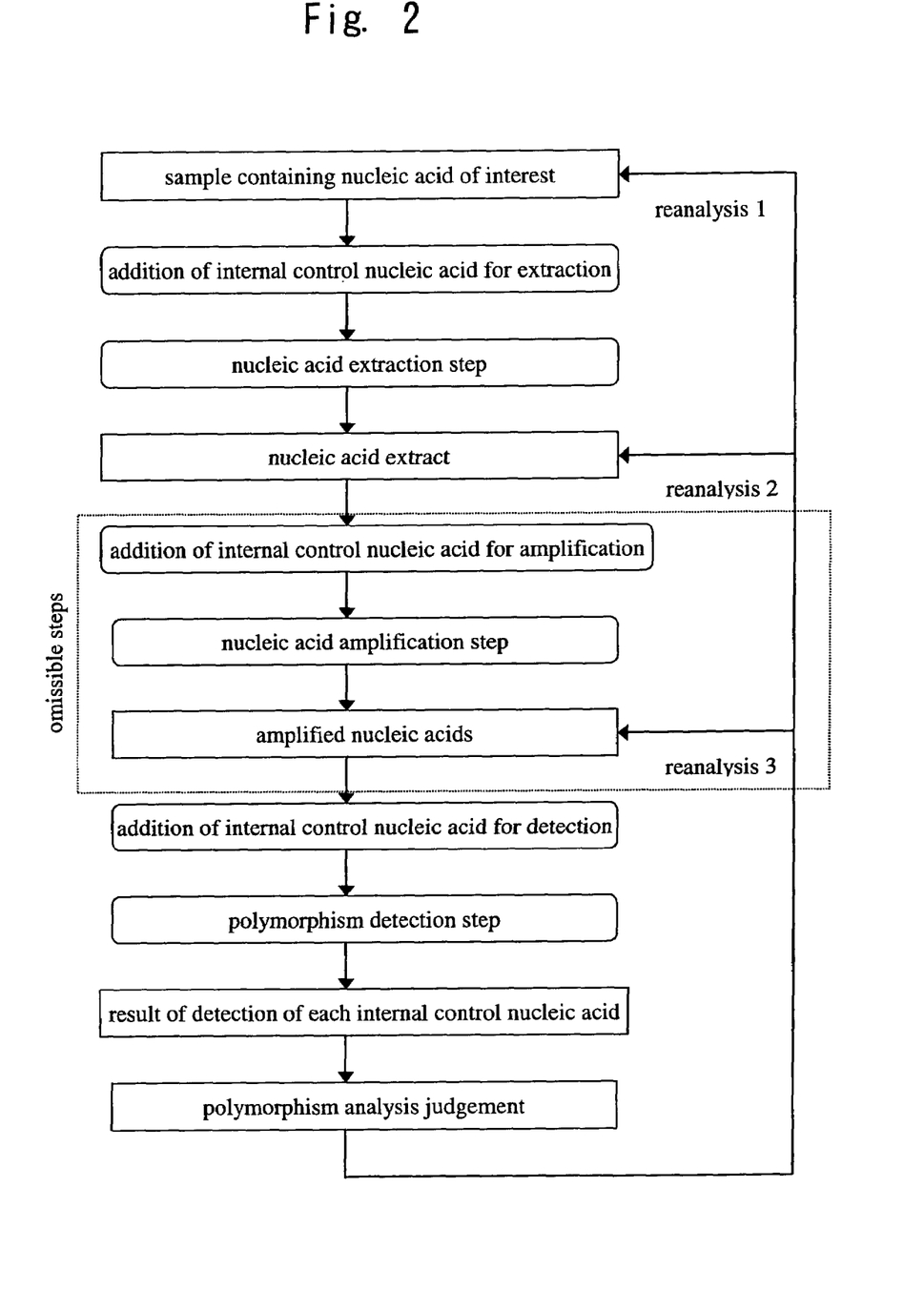
FIG. 2 shows a flow chart of the method for analyzing a nucleic acid of the present invention.

It appears that the nucleic acid extraction step was not performed normally; accordingly, such cases are judged as "insufficient extraction", and the analysis is re-performed from the point "reanalysis I" shown in FIG. 2. Especially in cases where the nucleic acid of interest can not be detected, it is highly possible that it may be false negative. Alternatively, in cases where the nucleic acid of interest can be detected in the object sample, it may be possible that the internal control nucleic acid(s) for extraction and/or the addition mechanism of them are abnormal. Accordingly, the internal control nucleic acid(s) for extraction are replaced, or the addition mechanism of them is inspected, or both of these measures are taken, and the analysis is re-performed from the point "reanalysis 1" shown in FIG. 2.

Case 4 (A Case in which Both the Detections of the Internal Control Nucleic Acid(s) for Extraction and Those of the Internal Control Nucleic Acid(s) for Detection are Abnormal, or These Internal Control Nucleic Acids can not be Detected)

In cases where neither the internal control nucleic acid(s) for extraction nor the internal control nucleic acid(s) for detection are detected, it appears that neither the nucleic acid extraction step nor the nucleic acid detection step was performed normally. Accordingly, such cases are judged as "insufficient", and the analysis is re-performed from the point "reanalysis 1" shown in FIG. 2. In abnormal cases in which the results for internal control nucleic acid(s) for extraction are not "undetected", it appears that the nucleic acid detection step was not performed normally. Accordingly, such cases are judged as "insufficient", and the analysis is re-performed from the point "reanalysis 3" shown in FIG. 2. When a judgement of "success" cannot be obtained in this reanalysis, the analysis is re-performed again from the point "reanalysis 1". Furthermore, when the "success" judgement of case 1 cannot be obtained following reanalysis in cases 2 through 4, the reanalysis is repeated on the basis of the judgement results obtained.

In the nucleic acid extraction step of the present invention, various known methods such as the abovementioned protease K/phenol method, and methods utilizing the adsorption characteristics of nucleic acids on a solid phase, e.g., nucleic acid extraction methods using magnetic silica particles, silica particles, silica fibers or filters, and spin columns, micro-plates or the like containing these substances, may be appropriately used. However, the present invention is not particularly limited to these methods.

Methods which can be used in the nucleic acid detection step of the present invention include known methods such as single-stranded DNA conformational polymorphism (SSCP) or restriction enzyme fragment length polymorphism (RFLP) using gel electrophoresis, and microarray methods, DNA chip methods and bead array methods, as well as pyro-sequencing methods, invader methods, mass spectrometry methods, HPLC methods and the like. Any method may be utilized as long as this method is capable of detecting and discriminating between nucleic acids whose sequences differ by one or more nucleotides. Furthermore, in addition to being used to judge the success or failure of the respective analysis steps, the detection signals of the abovementioned internal control nucleic acids for extraction or internal control nucleic acids for detection can also be used in various types of data processing such as the determination of the object nucleic acid, measurement of the base length or correction of the detection signals or the like.

The abovementioned nucleic acid detection step includes sample pre-treatments that are necessary for nucleic acid detection, e.g., thermal denaturation, various types of labeling treatments and solvent replacement or the like. It is desirable that the addition of the internal control nucleic acid(s) for detection to the nucleic acid extract be performed prior to such pre-treatments.

Next, in the method for analyzing nucleic acid which includes a nucleic acid amplification step between the abovementioned extraction step and detection step, a fixed amount of one or more internal control nucleic acids for extraction which can be amplified simultaneously with the nucleic acid of interest, but whose sequences differ from that of the nucleic acid of interest by one or more nucleotides, are added to a sample containing the nucleic acid of interest, and a nucleic acid extraction step is performed. Then, a fixed amount of one or more internal control nucleic acids for amplification which can be amplified simultaneously with the nucleic acid of interest, but whose sequences differ by one or more nucleotides from that of the nucleic acid of interest and those of the internal control nucleic acid(s) for extraction, are added to the nucleic acid extract thus obtained, and a nucleic acid amplification step is performed. Next, a fixed amount of one or more internal control nucleic acids for detection whose sequences differ by one or more nucleotides from that of the nucleic acid of interest, those of the internal control nucleic acid(s) for extraction and those of the internal control nucleic acid(s) for amplification, are added to the amplified nucleic acid thus obtained, and a known nucleic acid detection step which is capable of detecting and discriminating between nucleic acids whose sequences differ by one or more nucleotides is performed.

Figure 3:
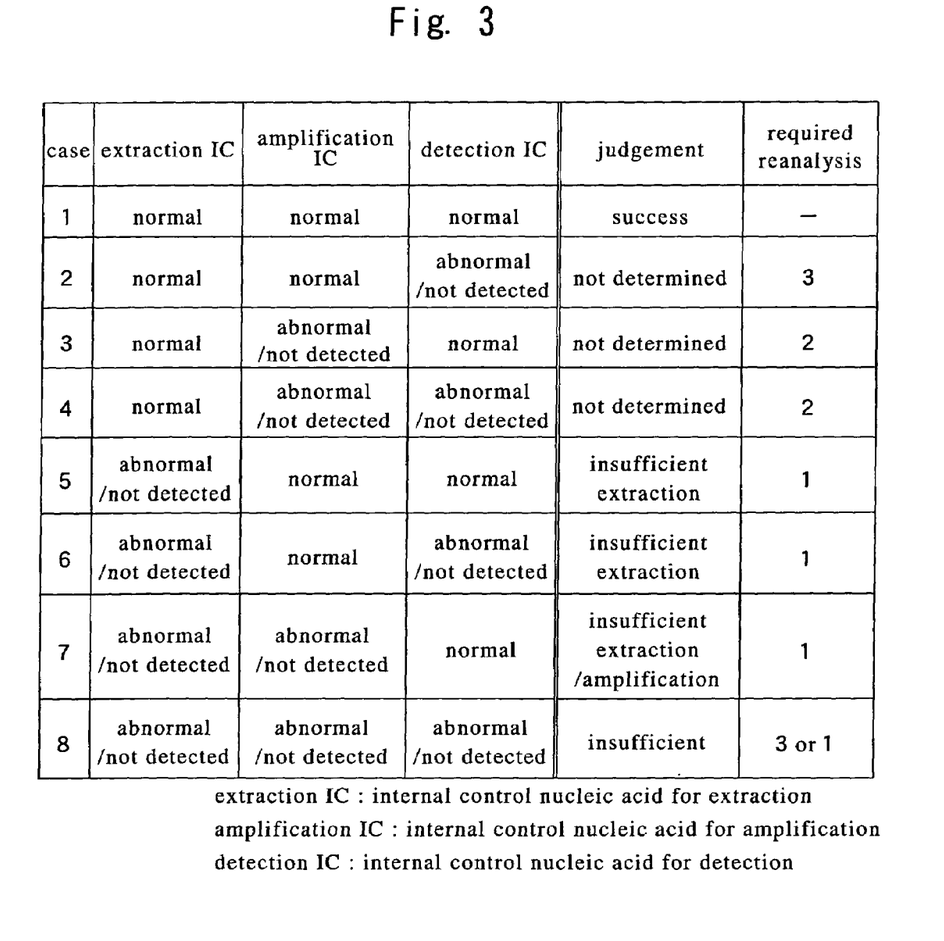
FIG. 3 shows a table for success-or-failure determination for the respective steps in the method of the present invention that includes an extraction step, an amplification step and a detection step.

As a result, as is shown in FIG. 3, the success or failure of the respective steps is judged in the same manner as described above, and the need for reanalysis is determined on the basis of these judgement results. Furthermore, false positives caused by contamination can be checked by treating a blank sample (control sample) which does not contain the nucleic acid of interest simultaneously with the nucleic acid of interest, and it facilitates the judgement of the need for reanalysis. In this case, it is judged that contamination has occurred if the object nucleic acid is detected in the blank sample, and analysis must be re-performed following a cleaning operation regardless of the detection results obtained for the internal control nucleic acid(s) for extraction and internal control nucleic acid(s) for detection.

The nucleic acid amplification method which may be appropriately used includes, but limited to, known methods such as a polymerase chain reaction (PCR), nucleic acid sequence-based amplification (NASBA). In cases where an amplification step is included, the quantities of internal control nucleic acid(s) for extraction and internal control nucleic acid(s) for amplification that are amplified simultaneously with the nucleic acid of interest can be decreased compared to those of internal control nucleic acid(s) for detection. However, the desirable relative ratio of quantities varies according to the amplification method and detection method used, and is not particularly limited.

Below, the relationship between the detection results for the internal control nucleic acid(s) for extraction, those for amplification and those for detection, and the judgement of the success or failure of the respective steps will be described with reference to FIG. 3.

Case 1 (A Case in which the Detections of the Internal Control Nucleic Acid(s) for Extraction, Those for Amplification and Those for Detection are all Normal)

It is judged that the respective steps were performed normally, and that the nucleic acid analysis operation performed for the nucleic acid of interest was "success"

Case 2 (A Case in which the Detections of the Internal Control Nucleic Acid(s) for Extraction and Those for Amplification are Normal, While the Detections of the Internal Control Nucleic Acid(s) for Detection are Abnormal, or the Last Nucleic Acid(s) are not Detected)

In cases where the nucleic acid of interest is not detected in the blank sample, it is highly probable that the nucleic acid analysis operation for the nucleic acid of interest was performed normally. However, there is a possibility that the internal control nucleic acid(s) for detection and/or the addition mechanism of them are abnormal. Consequently, such cases are judged as "not determined". Accordingly, the internal control nucleic acid(s) for detection are replaced, or the addition mechanism of them is inspected, or both of these measures are taken, and the analysis is re-performed from the point "reanalysis 3" shown in FIG. 2.

Case 3 (A Case in which the Detections of the Internal Control Nucleic Acid(s) for Extraction and Those for Detection are Normal, while the Detections of the Internal Control Nucleic Acid(s) for Amplification are Abnormal, or the Last Nucleic Acid(s) are not Detected)

In cases where the nucleic acid of interest is not detected in the blank sample, it is highly probable that the nucleic acid analysis operation for the nucleic acid of interest was performed normally. However, there is a possibility that the internal control nucleic acid(s) for amplification and/or the addition mechanism of them are abnormal. Consequently, such cases are judged as "not determined". Accordingly, the internal control nucleic acid(s) for amplification are replaced, or the addition mechanism of them is inspected, or both of these measures are taken, and the analysis is re-performed from the point "reanalysis 2" shown in FIG. 2.

Case 4 (A Case in which the Detections of the Internal Control Nucleic Acid(s) for Extraction are Normal, While the Detections of the Internal Control Nucleic Acid(s) for Amplification and Those for Detection are Abnormal, or these Internal Control Nucleic Acids are not Detected)

In cases where the nucleic acid of interest is not detected in the blank sample; it is highly probable that the nucleic acid analysis operation for the nucleic acid of interest was performed normally; however, there is a possibility that the internal control nucleic acid(s) for amplification and/or the addition mechanism of them, and the internal control nucleic acid(s) for detection and/or the addition mechanism of them, are abnormal. Consequently, such cases are judged as "not determined". Accordingly, the internal control nucleic acid(s) for amplification and/or the addition mechanism of them, and the internal control nucleic acid(s) for detection and/or the addition mechanism of them, are replaced or inspected, and the analysis is re-performed from the point "reanalysis 2" shown in FIG. 2.

Case 5 (A Case in which the Detections of the Internal Control Nucleic Acid(s) for Extraction are Abnormal or they are not Detected, While the Detections of the Internal Control Nucleic Acid(s) for Amplification and Those for Detection are Normal)

It appears that the nucleic acid extraction step was not performed normally; accordingly, this case is judged as "insufficient extraction", and the analysis is re-performed from the point "reanalysis 1" shown in FIG. 2. Especially in cases where the nucleic acid of interest can not be detected, there is an extremely high probability of a false negative. Furthermore, in cases where the nucleic acid of interest is detected in the object sample, there is a possibility that the internal control nucleic acid(s) for extraction and/or the addition mechanism of them are abnormal. Accordingly, the internal control nucleic acid(s) for extraction are replaced, or the addition mechanism of them is inspected, or both of these measures are taken, and the analysis is re-performed from the point "reanalysis 1" shown in FIG. 2.

Case 6 (A Case in which the Detections of the Internal Control Nucleic Acid(s) for Extraction and Those for Detection are Abnormal, or These Internal Control Nucleic Acids are not Detected, While the Detections of the Internal Control Nucleic Acid(s) for Amplification are Normal)

It appears that the nucleic acid extraction step was not performed normally, so that this case is judged as "insufficient extraction". Furthermore, there is a possibility that the internal control nucleic acid(s) for detection and/or the addition mechanism of them are abnormal. Accordingly, the internal control nucleic acid(s) for detection are replaced, or the addition mechanism of them is inspected, or both of these measures are taken, and the analysis is re-performed from the point "reanalysis 1" shown in FIG. 2. Furthermore, in cases where the nucleic acid of interest is detected in the object sample, there is a possibility that the internal control nucleic acid(s) for extraction and/or the addition mechanism of them, and the internal control nucleic acid(s) for detection and/or the addition mechanism of them, are abnormal. Accordingly, the internal control nucleic acid(s) for extraction and/or the addition mechanism of them, and the internal control nucleic acid(s) for detection and/or the addition mechanism of them, are replaced or inspected, and the analysis is re-performed from the point "reanalysis 1" shown in FIG. 2.

Case 7 (A Case in which the Detections of the Internal Control Nucleic Acid(s) for Extraction and Those for Amplification are Abnormal, or These Internal Control Nucleic Acids are not Detected, While the Detections of the Internal Control Nucleic Acid(s) for Detection are Normal)

The amplification step and/or the extraction step were not performed normally. Accordingly, this case is judged as "insufficient extraction/amplification", and the analysis is re-performed from the point "reanalysis 1" shown in FIG. 2. In cases where the nucleic acid of interest is detected in the object sample, there is a possibility that the internal control nucleic acid(s) for extraction and/or the addition mechanism of them, and the internal control nucleic acid(s) for amplification and/or the addition mechanism of them are abnormal. Accordingly, the internal control nucleic acid(s) for extraction and/or the addition mechanism of them, and the internal control nucleic acid(s) for amplification and/or the addition mechanism of them, are replaced or inspected, and the analysis is re-performed from the point "reanalysis 1" shown in FIG. 2.

Case 8 (A Case in which the Detections of the Internal Control Nucleic Acid(s) for Extraction, Those for Amplification and those for Detection are all Abnormal, or these Internal Control Nucleic Acids are not Detected)

In cases where the internal control nucleic acid(s) for extraction, those for amplification and those for detection are all undetected, it would appear that the nucleic acid extraction step, amplification step and detection step were not performed normally. Accordingly, such cases are judged as "insufficient", and the analysis is re-performed from the point "reanalysis 1" shown in FIG. 2. In abnormal cases in which the neither the internal control nucleic acid(s) for extraction nor the internal control nucleic acid(s) for amplification are undetected, it appears that the nucleic acid detection step may not be performed normally. Accordingly, such cases are judged as "insufficient", and the analysis is re-performed from the point "reanalysis 3" shown in FIG. 2. When a judgement of "success" cannot be obtained in the reanalysis, the analysis is re-performed again from the point "reanalysis 1".

Furthermore, when the "success" judgement of case 1 cannot be obtained following reanalysis in cases 2 through 8, the reanalysis is repeated on the basis of the judgement results obtained.

Since the abovementioned internal control nucleic acids are added in fixed amounts, i.e., known concentrations, various types of data processing such as determination of the object nucleic acid, measurement of the base length, and correction of the detection signals or the like, can be performed on the basis of the magnitudes of the detection signals obtained for the internal control nucleic acids.

In regard to means of amplifying the internal control nucleic acids simultaneously with the nucleic acid of interest, a widely known method in which sequences of primers called common primer pair which are identical to the sequences included in the nucleic acid of interest is included in the internal control nucleic acid(s), is superior in terms of economy and amplification stability; however, the method of the present invention can also be performed using a plurality of independent primer pairs.

It is necessary that the sequences of the internal control nucleic acids differ by one or more nucleotides from the sequence of the nucleic acid of interest. However, in cases where an amplification step is included, or in cases where a DNA chip utilizing hybridization or the like is used in the detection step, a higher sequence similarity with the object nucleic acid makes it easier to obtain a comparable amplification efficiency and binding efficiency; accordingly, such a method is superior in terms of reproducibility and is preferable for use.

The present invention further provides a kit which is used to perform the above-mentioned method for analyzing nucleic acid of the present invention, the kit comprising:
  (i) internal control nucleic acid(s) for extraction and/or extraction reagent(s) containing internal control nucleic acid(s) for extraction, and
  (ii) internal control nucleic acid(s) for detection and/or detection reagent(s) containing internal control nucleic acid(s) for detection.

The present invention further provides a kit which is used to perform the above-mentioned method for analyzing nucleic acid of the present invention, the kit comprising:
  (i) internal control nucleic acid(s) for extraction and/or extraction reagent(s) containing internal control nucleic acid(s) for extraction,
  (ii) internal control nucleic acid(s) for detection and/or detection reagent(s) containing internal control nucleic acid(s) for detection, and
  (iii) internal control nucleic acid(s) for amplification and/or amplification reagents containing internal control nucleic acid(s) for amplification.

In the kits, the respective internal control nucleic acids may be included alone in the kit. However, these internal control nucleic acids may also be included together with other reagents required in the respective steps, such as solvents, labeling reagents, primers or the like. Respective components that may be contained in the reagents will readily be recognized by a person skilled in the art, and there are no particular restrictions on such components.

Furthermore, the kit of the present invention is characterized in that the above-mentioned internal control nucleic acids for extraction are fixed quantities of nucleic acids whose sequences differ by one or more nucleotides from the sequence of the nucleic acid of interest, and the above-mentioned internal control nucleic acids for detection are fixed quantities of nucleic acids whose sequences differ by one or more nucleotides from both the sequence of the nucleic acid of interest and the sequences of the above-mentioned internal control nucleic acids for extraction.

Furthermore, in cases where the kit contains internal control nucleic acid(s) for amplification and/or amplification reagent(s) containing internal control nucleic acid(s) for amplification, the above-mentioned internal control nucleic acids for extraction are fixed quantities of nucleic acids which can be amplified simultaneously with the nucleic acid of interest, but whose sequences differ by one or more nucleotides from that of the nucleic acid of interest, the above-mentioned internal control nucleic acids for amplification are fixed quantities of nucleic acids which can be amplified simultaneously with the nucleic acid of interest, but whose sequences differ by one or more nucleotides from that of the nucleic acid of interest and those of the internal control nucleic acids for extraction, and the internal control nucleic acids for detection are fixed quantities of nucleic acids whose sequences differ by one or more nucleotides from that of the nucleic acid of interest, those of the internal control nucleic acids for extraction and those of the internal control nucleic acids for amplification.

As a result, when the method of the present invention is performed using the kit of the present invention, a detection method which is capable of discriminating between nucleic acids whose sequences differ by one or more nucleotides can be used. Furthermore, various types of data processing such as determination of the nucleic acid of interest, measurement of the base length, and correction of the detection signals or the like, can be performed using the detection results obtained for the internal control nucleic acids.

BEST MODE FOR CARRYING OUT THE INVENTION

A flow chart illustrating an embodiment of the present invention is shown in FIG. 2.

To a sample containing a nucleic acid of interest, such as human blood or other body fluid, tissues or cells, bacteria, viruses or the like, internal control nucleic acid(s) for extraction and/or extraction reagent(s) containing internal control nucleic acid (s) for extraction are added to the sample, after which an extraction step is performed in which the nucleic acid of interest and the internal control nucleic acid(s) for extraction are simultaneously extracted.

Next, internal control nucleic acid(s) for detection and/or detection reagent(s) containing internal control nucleic acid (s) for detection are added to the nucleic acid extract thus obtained, after which a detection step is performed in which the nucleic acid of interest, the internal control nucleic acid(s) for extraction and the internal control nucleic acid(s) for detection are detected and respectively discriminated.

Then, the success or failure of the respective steps is judged as described above from the detection results obtained for the respective internal control nucleic acids, and the analysis is re-performed from the abovementioned extraction step or detection step on the basis of the judgement results.

Alternatively, to a sample containing the nucleic acid of interest, internal control nucleic acid(s) for extraction and/or extraction reagent(s) containing internal control nucleic acid (s) for extraction are added to the sample, after which an extraction step is performed in which the nucleic acid of interest and the internal control nucleic acid(s) for extraction are simultaneously extracted.

Next, internal control nucleic acid(s) for amplification and/or detection reagent(s) containing internal control nucleic acid(s) for amplification are added to the nucleic acid extract thus obtained, after which an amplification step is performed in which the nucleic acid of interest, the internal control nucleic acid(s) for extraction and the internal control nucleic acid(s) for amplification are simultaneously amplified.

Then, internal control nucleic acid(s) for detection and/or detection reagent(s) containing internal control nucleic acid (s) for detection are added to the amplified nucleic acid thus obtained, after which a detection step is performed in which the nucleic acid of interest, the internal control nucleic acid(s) for extraction, the internal control nucleic acid(s) for detection and the internal control nucleic acid(s) for amplification are detected and respectively discriminated. Next, the success or failure of the respective steps is judged as described above from the detection results obtained for the respective internal control nucleic acids, and the analysis is re-performed from the abovementioned extraction step, amplification step or detection step on the basis of the judgement results.

Figure 4:
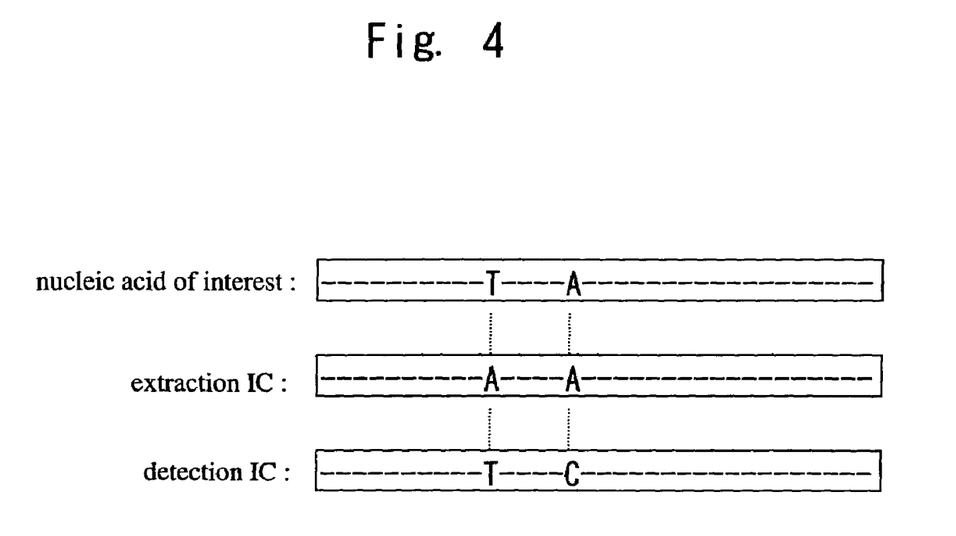
FIG. 4 shows one example of internal control nucleic acids for extraction and internal control nucleic acids for detection in the present invention.

One example of the internal control nucleic acids used in the present invention is shown in FIG. 4. Specifically, these are examples of internal control nucleic acids used when a fixed amount of internal control nucleic acid(s) for extraction whose sequences differ by one or more nucleotides from that of the nucleic acid of interest are added to a sample containing the nucleic acid of interest, after which a nucleic acid extraction step is performed, and a fixed amount of internal control nucleic acid(s) for detection whose sequences differ by one or more nucleotides from that of the nucleic acid of interest and those of the internal control nucleic acid(s) for extraction are added to the nucleic acid extract thus obtained, after which a nucleic acid detection step that is capable of detecting and discriminating between nucleic acids whose sequences differ by one or more nucleotides is performed. The base lengths of the nucleic acid of interest, the internal control nucleic acid(s) for extraction and the internal control nucleic acid(s) for detection are the same. A nucleic acid having adenine (A) as a nucleotide at a specified position which is thymine (T) in the nucleic acid of interest, and thus having a nucleotide sequence that differs from the nucleic acid of interest by one nucleotide, is utilized as an internal control nucleic acid for extraction (extraction IC). Similarly, a nucleic acid having cytosine (C) as a nucleotide at another specified position which is A in the nucleic acid of interest, and thus having a nucleotide sequence that differs from the nucleic acid of interest by one nucleotide, is utilized as an internal control nucleic acid for detection (detection IC). In this case, the extraction IC and the detection IC are nucleic acids with nucleotide sequences that differ by two nucleotides, and are therefore detected as different signals by a detector that is capable of detecting and discriminating between nucleic acids whose sequences differ by one or more nucleotides.

Figure 5:
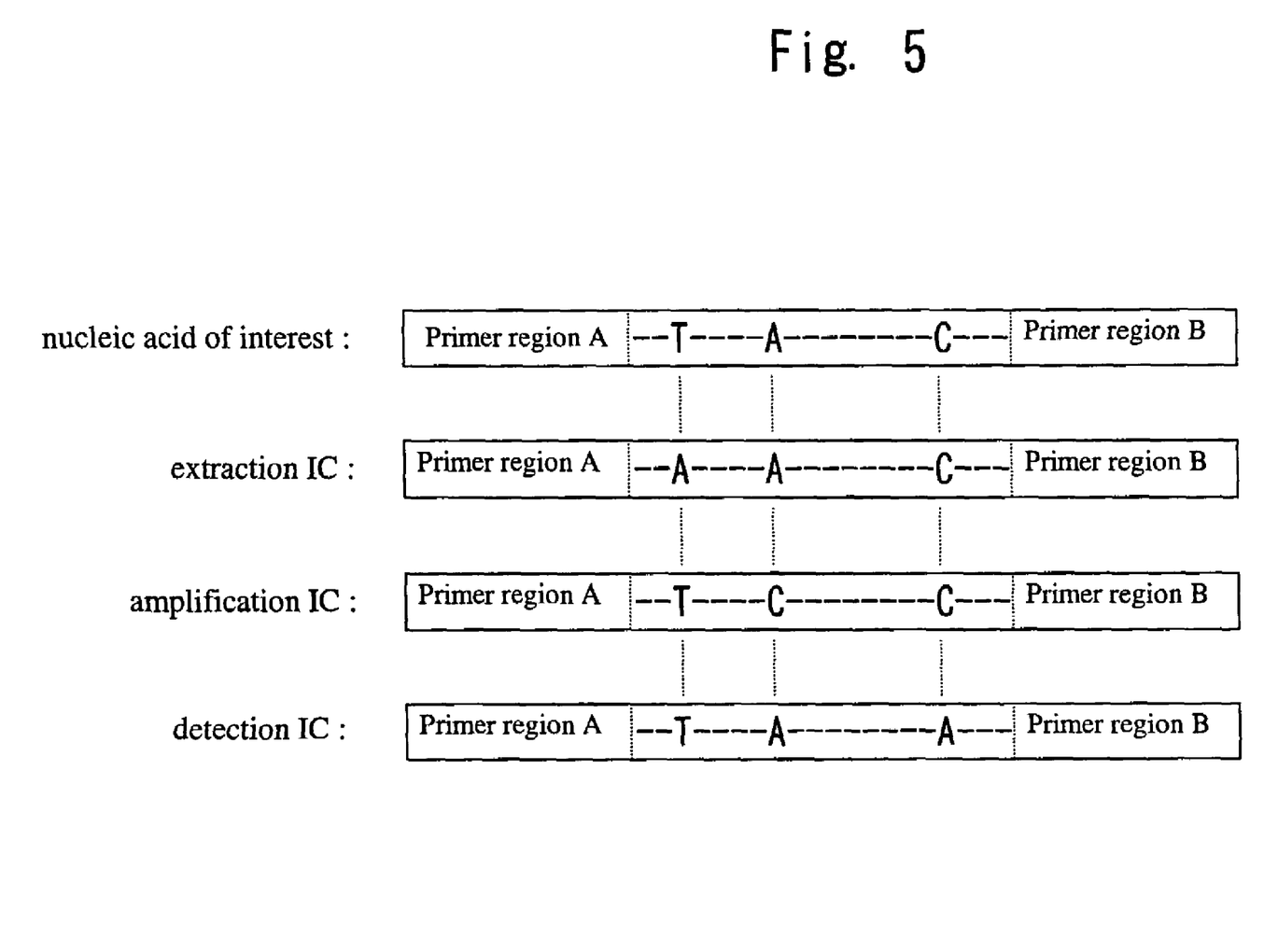
FIG. 5 shows one example of internal control nucleic acids for extraction, internal control nucleic acids for amplification and internal control nucleic acids for detection in the present invention.

Another example of internal control nucleic acids used in the method for analyzing a nucleic acid in which a nucleic acid amplification step is included between the extraction step and the detection step is shown in FIG. 5. In this case, the method of the present invention is performed as follows. A fixed amount of internal control nucleic acid(s) for extraction which can be amplified simultaneously with the nucleic acid of interest, but whose sequences differ by one or more nucleotides from that of the nucleic acid of interest, are added to a sample containing the nucleic acid of interest, and a nucleic acid extraction step is performed. Next, a fixed amount of internal control nucleic acid(s) for amplification which can be amplified simultaneously with the nucleic acid of interest, but whose sequences differ by one or more nucleotides from that of the nucleic acid of interest and those of the internal control nucleic acid(s) for extraction, are added to the nucleic acid extract thus obtained, and a nucleic acid amplification step is performed. Afterward, a fixed amount of internal control nucleic acid(s) for detection whose sequences differ by one or more nucleotides from that of the nucleic acid of interest and those of the internal control nucleic acid(s) for extraction and internal control nucleic acid(s) for amplification, are added to the amplified nucleic acid thus obtained, and a nucleic acid detection step which is capable of discriminating between nucleic acids whose sequences differ by one or more nucleotides is performed.

Furthermore, as a means of amplifying the internal control nucleic acids simultaneously with the nucleic acid of interest in the amplification step, a widely known method in which sequences of a pair of primers called common primer pair which are identical to the nucleotide sequences included in the nucleic acid of interest is included in the internal control nucleic acids, is used.

As shown in FIG. 5, a nucleic acid having A as a nucleotide at a specified position which is T in the nucleic acid of interest, and thus having a nucleotide sequence that differs from the nucleic acid of interest by one nucleotide, is utilized as an internal control nucleic acid for extraction (extraction IC). Similarly, a nucleic acid having C as a nucleotide at another specified position which is A in the nucleic acid of interest, and thus having a nucleotide sequence that differs from the nucleic acid of interest by one nucleotide, is utilized as an internal control nucleic acid for amplification (amplification IC). Furthermore, a nucleic acid having A as a nucleotide at still another specified position which is C in the nucleic acid of interest, and thus having a nucleotide sequence that differs from the nucleic acid of interest by one nucleotide, is utilized as an internal control nucleic acid for detection (detection IC). In this case, the detection IC, amplification IC and detection IC are nucleic acids with nucleotide sequences that respectively differ by two nucleotides one another. Accordingly, these nucleic acids can be detected as different signals by a detector that is capable of detecting and discriminating between nucleic acids whose sequences differ by one or more nucleotides. Since both primer region A and primer region B which exist on both sides of the regions showing differences in the abovementioned nucleotide sequences are the same nucleotide sequences in the nucleic acid of interest and the respective internal control nucleic acids, the respective nucleotide sequences can be amplified by one type of primer pair.

Figure 6:
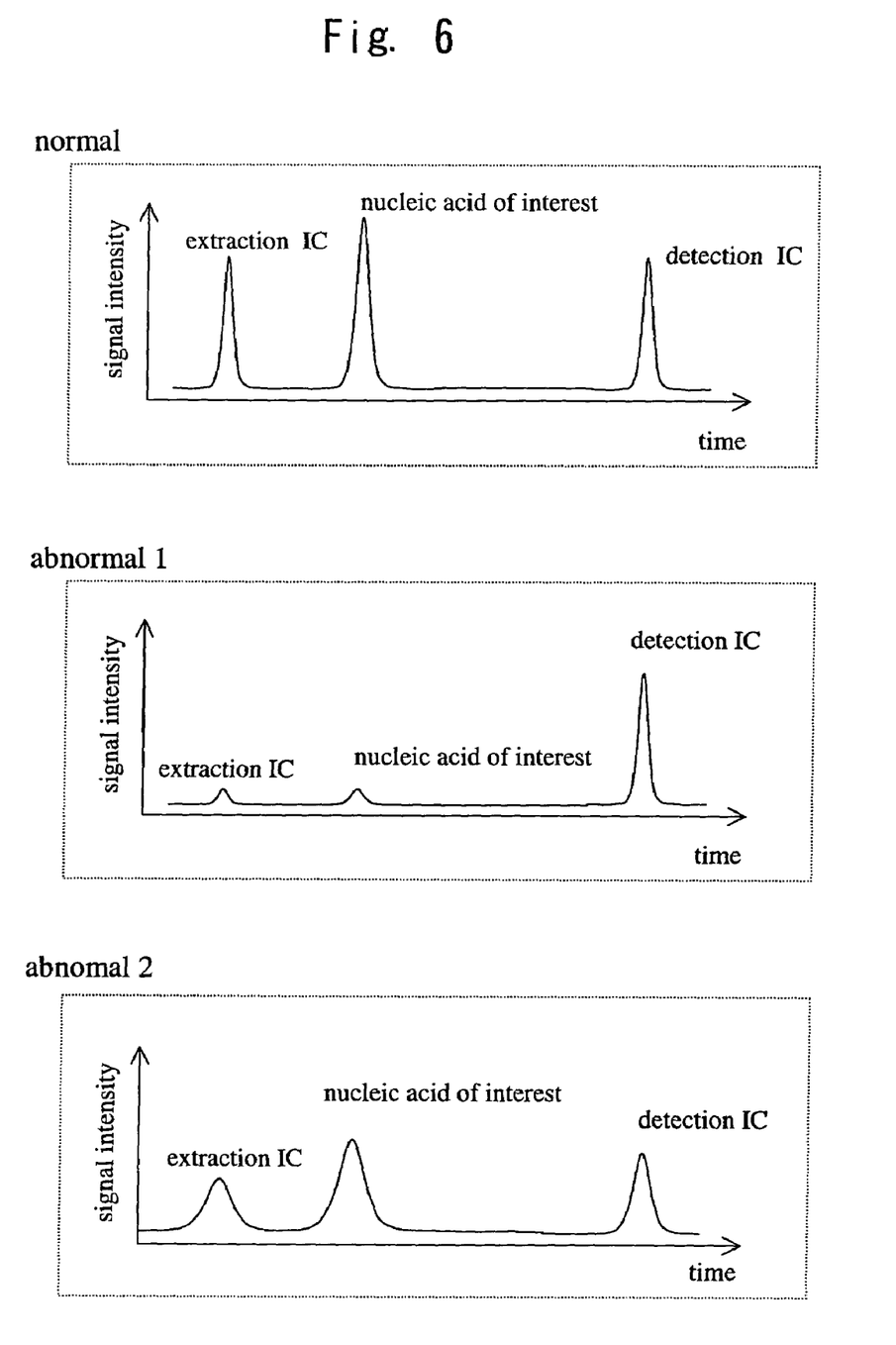
FIG. 6 shows one example of detection results obtained in the method of the present invention performed in order to detect single-stranded DNA conformational polymorphism using gel electrophoresis in the detection step.

One example of the results obtained when the method for analyzing a nucleic acid of the present invention was performed is shown in FIG. 6. FIG. 6 shows an example of electrophoresis chromatograms that were obtained in a case where single-stranded DNA conformational polymorphism (SSCP) analysis using gel electrophoresis was performed as a nucleic acid detection step capable of detecting and discriminating between nucleic acids whose sequences differ by one or more nucleotides, utilizing a fixed amount of an internal control nucleic acid for extraction with a sequence differing by one or more nucleotides from that of the nucleic acid of interest, and a fixed amount of an internal control nucleic acid for detection with a sequence differing by one or more nucleotides from that of the nucleic acid of interest and that of the internal control nucleic acid for extraction, for a sample containing the nucleic acid of interest. In this SSCP, a capillary gel electrophoresis apparatus was used; the respectively fluorescent-labeled object nucleic acid, extraction IC and detection IC were excited by means of a laser, and the fluorescent spectrum was measured with a CCD camera.

As shown in FIG. 6, the case of "normal" is an exemplarly chromatogram that was obtained when expected peak intensities were respectively obtained for the extraction IC, object nucleic acid and detection IC, indicating that the analysis process was performed normally. On the other hand, the case of "abnormal 1" is one example of case 3 shown in FIG. 1. The fluorescence peak of the extraction IC is extremely low, indicating that the extraction IC is abnormal, while the fluorescence peak of the detection IC shows a comparable fluorescent intensity at the same detection time as a normal case, so that this peak is normal. Accordingly, this case is judged as "insufficient extraction", and "reanalysis 1" shown in FIG. 2 is performed. The case of "abnormal 2" is one example of case 4 shown in FIG. 1. The fluorescence peaks of the extraction IC and the detection IC are broadened, so that these ICs are abnormal even if they are not undetected. In particular, since the fluorescence peak of the nucleic acid of interest is also broadened in this case, it appears that the function of nucleic acid separation by electrophoresis has dropped, so that "reanalysis 3" shown in FIG. 2 is performed.

Figure 7A:
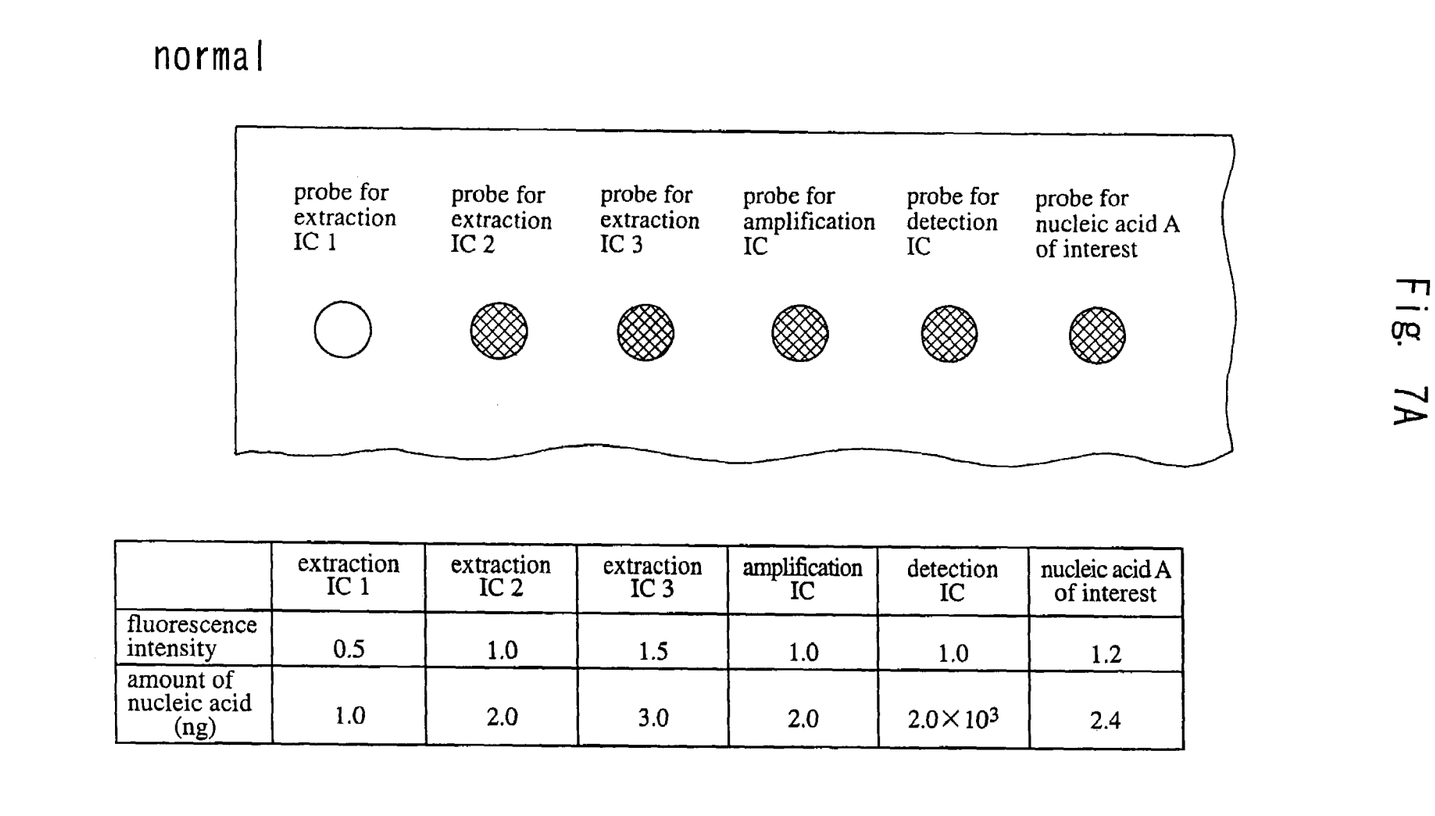
FIGS. 7A and 7B show one example of detection results obtained in the method of the present invention in a quantitative analysis using a DNA chip in the detection step.
Figure 7B:
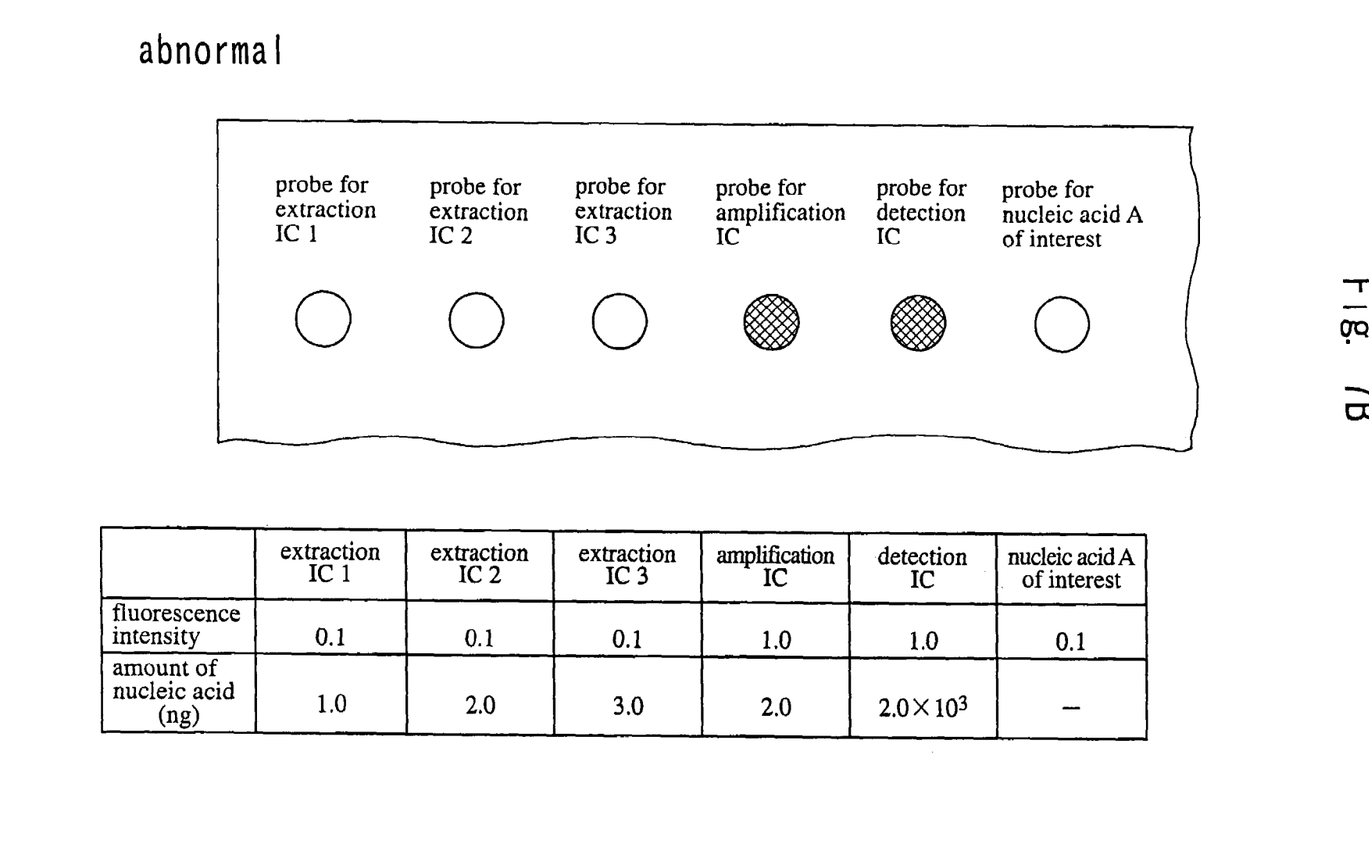

Next, one example of the results obtained in the method for analyzing a nucleic acid of the present invention using a DNA chip is shown in FIG. 7. Specifically, this example shows a case where a DNA chip was used in a nucleic acid detection step capable of detecting and discriminating between nucleic acids with sequences differing by one or more nucleotides, using a fixed amount of internal control nucleic acids for extraction which could be amplified simultaneously with nucleic acid of interest, but which had sequences differing by one or more nucleotides from that of the nucleic acid of interest, a fixed amount of an internal control nucleic acid for amplification which could be amplified simultaneously with nucleic acid of interest, but which had a sequence differing by one or more nucleotides from that of the nucleic acid of interest and those of the internal control nucleic acids for extraction, and a fixed amount of an internal control nucleic acid for detection which had a sequence differing by one or more nucleotides from that of the nucleic acid of interest, those of the internal control nucleic acids for extraction and that of the internal control nucleic acid for amplification.

Probes respectively containing nucleotide sequences complementary to those of the extraction IC 1, extraction IC 2, extraction IC 3, amplification IC, detection IC and nucleic acid A of interest were fixed to the surface of the DNA chip. The extraction IC 1, extraction IC 2, extraction IC 3, amplification IC, detection IC and nucleic acid A of interest, which were respectively labeled with fluorescent dyes, were hybridized on this DNA chip, and were detected by means of a DNA chip reader capable of measuring fluorescent spectra.

As shown in FIG. 7, the case of "normal" is an example of a case in which the expected peak intensities indicated in the table (0.5, 1.0 or 1.5) were obtained respectively for the extraction IC 1, extraction IC 2, extraction IC 3, amplification IC and detection IC, indicating that the analysis process was performed normally. In a case where the amount of the nucleic acid of interest is determined from the magnitudes of the detection signals of the internal control nucleic acids, a calibration curve for the nucleic acid concentration is prepared from the fluorescent intensities of extraction IC 1, extraction IC 2 and extraction IC 3 and known quantities of these nucleic acids, and the quantity of the nucleic acid A of interest can be determined as 2.4 ng from the fluorescent intensity of the nucleic acid of interest.

On the other hand, the case of "abnormal" is one example of case 5 shown in FIG. 3. The fluorescent intensities of extraction IC 1, extraction IC 2 and extraction IC 3 are respectively 0.1, and are thus lower than the expected fluorescent intensities of 0.5, 1.0 and 1.5, respectively, indicating that the extraction ICs are abnormal. The fluorescence peaks of amplification IC and detection IC shows the same intensities as the expected fluorescent intensities, and are therefore normal. In this case, the fact that the nucleic acid A of interest is not detected would appear to indicate a high probability of a false negative. Accordingly, this case is judged as "insufficient extraction", and "reanalysis 1" shown in FIG. 2 is performed.

An example of data processing in which the detection signals are corrected on the basis of the magnitudes of the detection signals for the respective internal control nucleic acids is shown in FIG. 8. Like FIG. 6, FIG. 8 shows an example of electrophoresis chromatograms that were obtained in a case where SSCP analysis using a capillary electrophoresis apparatus was performed as a nucleic acid detection step capable of detecting and discriminating between nucleic acids with sequences that differ by one or more nucleotides.

Figure 8A:
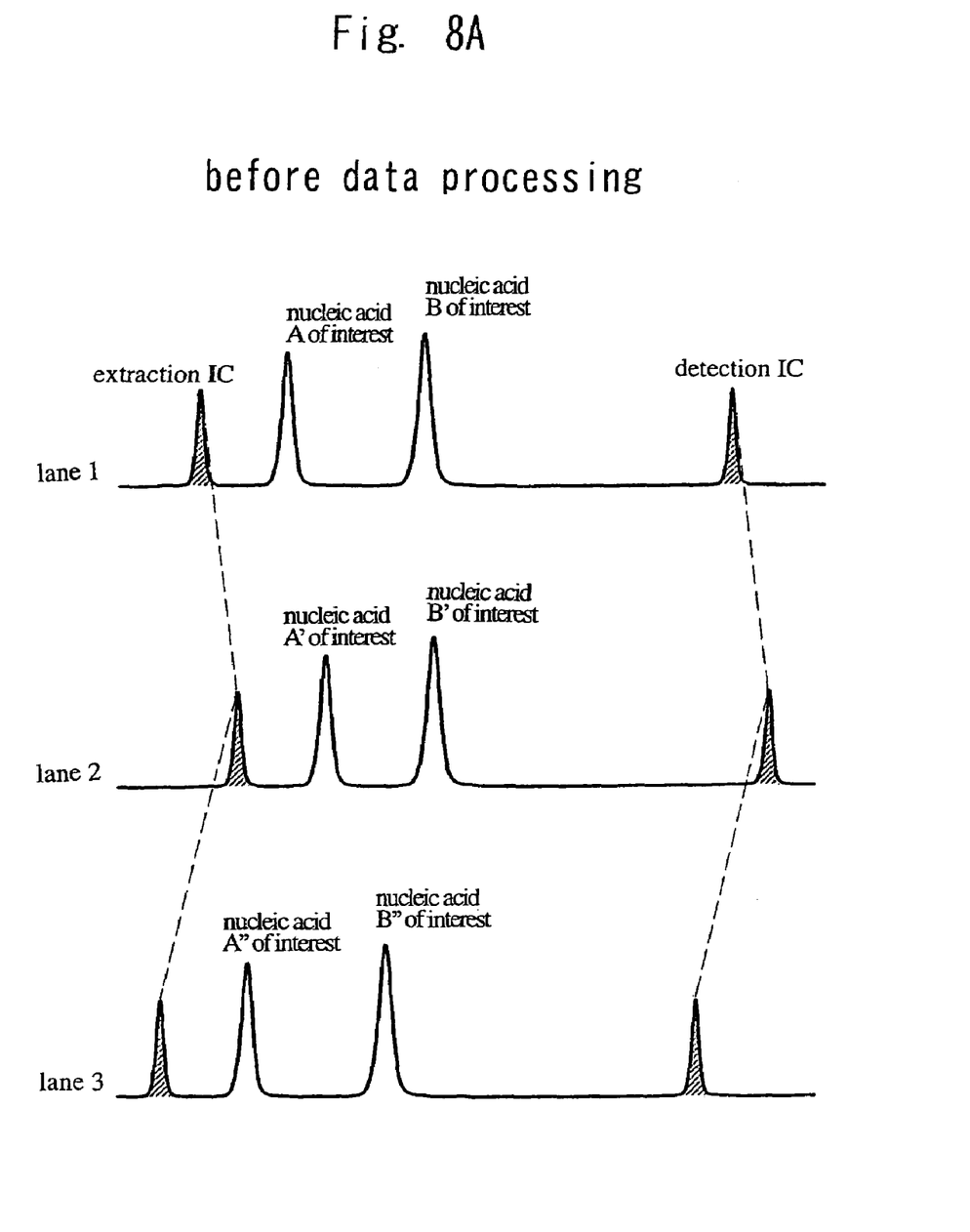
FIGS. 8A and 8B show one example of data processing used to detect single-stranded DNA conformational polymorphism using gel electrophoresis in the detection step of the method of the present invention.
Figure 8B:
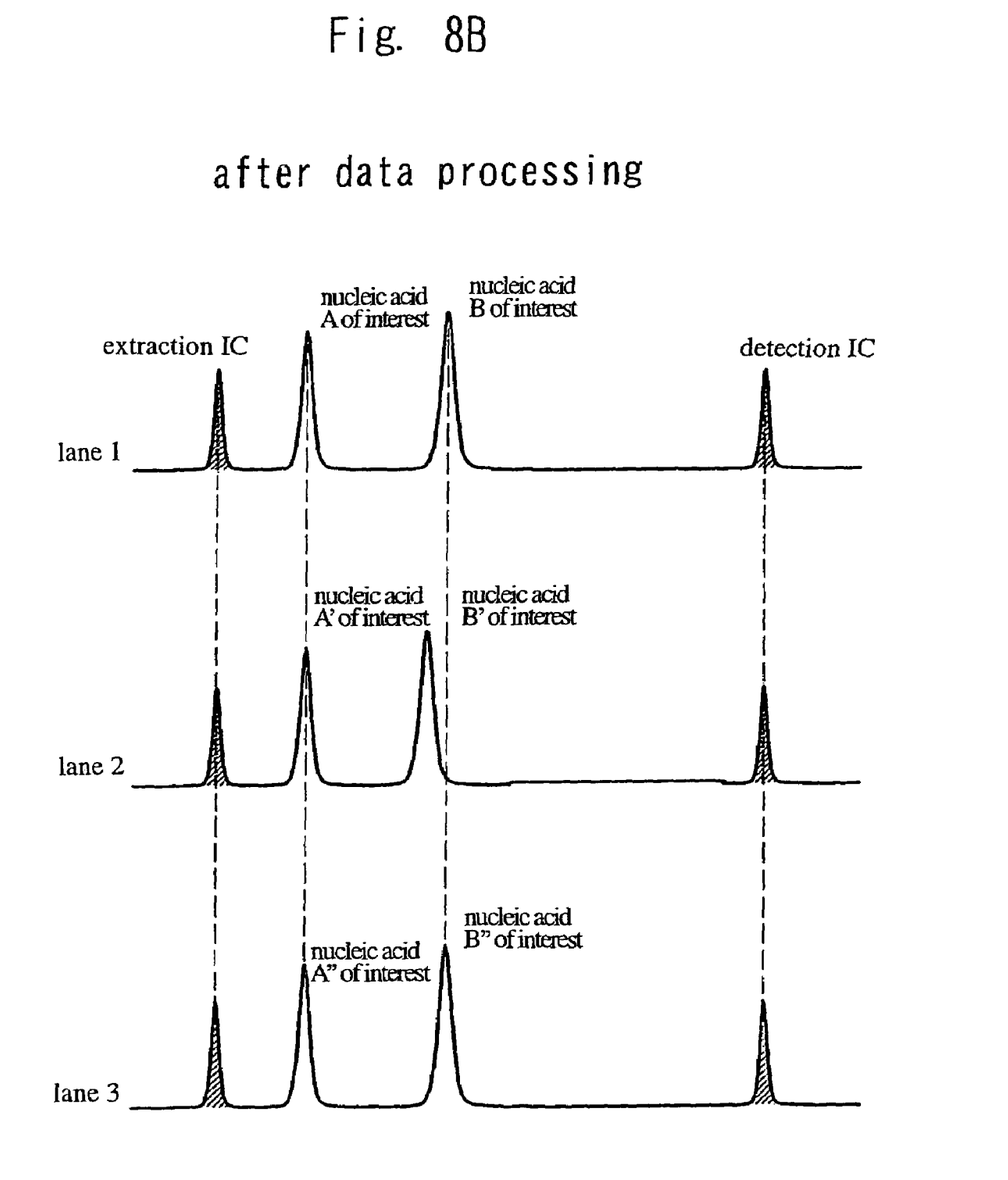

In the chromatograms shown before data processing, there is a shift in the detection time of the internal control nucleic acids between lanes. In such cases, it is difficult to judge at a glance whether the peak for nucleic acid A of interest is the same peak as A' or A", or whether the peak for nucleic acid B of interest is the same peak as B' or B". Accordingly, since the known internal control nucleic acids originally have the same detection time, the chromatograms can be corrected such that the extraction ICs or detection IC in the respective lanes have the same detection time, to result in the chromatograms after data processing. Such data processing make it possible to determine immediately that the peak for nucleic acid A of interest is the same peak as A' and A", and that the peak for nucleic acid B of interest is the same peak as B", while B' is a different peak.

INDUSTRIAL APPLICABILITY

The present invention makes it possible to judge the success or failure of the operations in the respective steps of extraction, amplification and detection that make up the nucleic acid analysis. The reliability of the analysis results obtained can be increased, and re-testing can be automated according to the present invention. In particular, this effect contributes to an improvement in the reliability of tests and diagnoses performed on the basis of genetic analysis in the medical field.

All publications, patents and patent applications cited herein are incorporated herein by reference in their entirety.

The invention claimed is:

1. A method for analyzing a nucleic acid comprising steps of extracting, amplifying, and detecting the nucleic acid of interest, wherein said method comprises the steps of:
obtaining a sample;
adding an internal control for extraction to the sample;
extracting the nucleic acid;
adding an internal control for amplification to the sample subsequent to the step of extracting, wherein the internal control for amplification is different from the internal control for extraction and an internal control for detection;
amplifying the nucleic acid;
adding the internal control for detection to the sample subsequent to the step of amplifying, wherein the internal control for detection is different from the internal control for extraction and the internal control for amplification;
detecting the nucleic acid in the sample;
judging the success or failure of each of the steps of extracting, amplifying, and detecting from detection results obtained for each of said internal controls, and wherein the step of judging the success or failure of the steps of extracting, amplifying and detecting includes the step of judging whether detection results for each of the internal controls is abnormal or undetected, or normal; and
re-performing the above-mentioned steps from any of the steps which are judged as insufficient, such that analysis is re-performed from any one of the steps which are judged as insufficient based on the judgments of the success or failure of said nucleic acid extraction step, amplification step and detection step; and
wherein the success or failure of said steps is judged from peak broadness together with peak intensity and shift in retention time of said respective internal control nucleic acids.

2. A method for analyzing a nucleic acid comprising steps of extracting the nucleic acid of interest and detecting nucleic acids by electrophoresis, wherein said method comprises:
(a) a nucleic acid extraction step in which nucleic acids are extracted after one or more internal control nucleic acids for extraction, which can be detected while being discriminated from said nucleic acid of interest, have been added to a sample containing said nucleic acid of interest;
(b) a nucleic acid detection step in which nucleic acids are detected after one or more internal control nucleic acids for detection, which can be detected while being discriminated from said nucleic acid of interest and from internal control nucleic acids for extraction, have been added to a sample containing nucleic acids extracted in said step (a), and wherein said nucleic acid detection step includes the step of obtaining an electrophoresis chromatogram; and
(c) a step in which the success or failure of said extraction and detection steps is judged from peak broadness of said respective internal control nucleic acids which is observed in said electrophoresis chromatogram obtained in said step (b); and
wherein the success or failure of said steps is judged from the peak broadness together with peak intensity and shift in retention time of said respective internal control nucleic acids.

3. A method for analyzing a nucleic acid comprising steps of extracting and amplifying the nucleic acid of interest, and detecting nucleic acids by electrophoresis, wherein said method comprises:
(a) a nucleic acid extraction step in which nucleic acids are extracted after one or more internal control nucleic acids for extraction, which can be detected while being discriminated from said nucleic acid of interest, have been added to a sample containing the nucleic acid of interest;
(b) a nucleic acid amplification step in which nucleic acids are amplified after one or more internal control nucleic acids for amplification, which can be detected while being discriminated from said nucleic acid of interest and from said internal control nucleic acids for extraction, have been added to a sample containing nucleic acids extracted in said step (a);
(c) a nucleic acid detection step in which nucleic acids are detected after one or more internal control nucleic acids for detection, which can be detected while being discriminated from said nucleic acid of interest, said internal control nucleic acids for extraction and said internal control nucleic acids for amplification, have been added to a sample containing nucleic acids amplified in said step (b), and wherein said nucleic acid detection step includes the step of obtaining an electrophoresis chromatogram; and (d) a step in which the success or failure of said extraction, amplification and detection steps is judged from peak broadness of said respective internal control nucleic acids which is observed in said electrophoresis chromatogram obtained in said step (c); and wherein the success or failure of said steps is judged from the peak broadness together with peak intensity and shift in retention time of said respective internal control nucleic acids.

4. A method for analyzing a nucleic acid comprising steps of extracting and amplifying the nucleic acid of interest, and detecting nucleic acids by electrophoresis, wherein said method comprises:

(a) a nucleic acid extraction step in which nucleic acids are extracted after one or more internal control nucleic acids for extraction, which can be detected while being discriminated from said nucleic acid of interest, have been added to a sample containing the nucleic acid of interest;

(b) a nucleic acid amplification step in which nucleic acids are amplified after one or more internal control nucleic acids for amplification, which can be detected while being discriminated from said nucleic acid of interest and from said internal control nucleic acids for extraction, have been added to a sample containing nucleic acids extracted in said step (a);

(c) a nucleic acid detection step in which nucleic acids are detected after one or more internal control nucleic acids for detection, which can be detected while being discriminated from said nucleic acid of interest, said internal control nucleic acids for extraction and said internal control nucleic acids for amplification, have been added to a sample containing nucleic acids amplified in said step (b), and wherein said nucleic acid detection step includes the step of obtaining an electrophoresis chromatogram; and (d) a step in which the success or failure of said extraction, amplification and detection steps is judged from peak broadness of said respective internal control nucleic acids which is observed in said electrophoresis chromatogram obtained in said step (c); and wherein the success or failure of said steps is judged from the peak broadness together with peak intensity and shift in retention time of said respective internal control nucleic acids; and wherein the retention time is the corrected retention time which is corrected based on the retention time of the internal control nucleic acids.

5. A nucleic acid analyzing method as in any one of claims 1, 2, 3, and 4, wherein the internal control nucleic acid for extraction differs from the nucleic acid of interest by one or more nucleotides; and wherein the internal control nucleic acid for detection differs from both the nucleic acid of interest and the internal control nucleic acid for extraction by one or more nucleotides.

6. A nucleic acid analyzing method according to claim 5, wherein base lengths of the nucleic acid of interest, the internal control nucleic acid for extraction, and the internal control nucleic acid for detection are the same.

7. A nucleic acid analyzing method as in any one of claims 1, 2, 3, and 4, wherein the detection of the nucleic acid of interest, the internal control nucleic acid for extraction, and the internal control nucleic acid for detection is analyzed by single-stranded DNA conformational polymorphism analysis.

8. The method according to claim 2 or 3, which further contains a step of re-performing wherein analysis is re-performed from any of the steps which are judged as insufficient based on the judgments of the success or failure of said steps.

* * * * *